(12) United States Patent
Van Oldenborgh et al.

(10) Patent No.: US 11,688,062 B2
(45) Date of Patent: Jun. 27, 2023

(54) MEDICAL DEVICE FOR TRANSCRIPTION OF APPEARANCES IN AN IMAGE TO TEXT WITH MACHINE LEARNING

(71) Applicant: Kepler Vision Technologies B.V., Amsterdam (NL)

(72) Inventors: Marc Jean Baptist Van Oldenborgh, Amsterdam (NL); Henricus Meinardus Gerardus Stokman, Amsterdam (NL); Ran Tao, Amsterdam (NL)

(73) Assignee: Kepler Vision Technologies B.V., Amsterdam (NL)

( * ) Notice: Subject to any disclaimer, the term of this patent is extended or adjusted under 35 U.S.C. 154(b) by 336 days.

(21) Appl. No.: 16/975,015

(22) PCT Filed: Mar. 23, 2020

(86) PCT No.: PCT/EP2020/058034
§ 371 (c)(1),
(2) Date: Aug. 21, 2020

(87) PCT Pub. No.: WO2020/188119
PCT Pub. Date: Sep. 24, 2020

(65) Prior Publication Data
US 2021/0233234 A1    Jul. 29, 2021

(30) Foreign Application Priority Data
Mar. 21, 2019 (EP) .................................... 19164480

(51) Int. Cl.
*G06T 7/00* (2017.01)
*G16H 10/60* (2018.01)
(Continued)

(52) U.S. Cl.
CPC ............ *G06T 7/0012* (2013.01); *G16H 10/60* (2018.01); *G16H 30/20* (2018.01); *G16H 30/40* (2018.01);
(Continued)

(58) Field of Classification Search
CPC ......... G06T 7/0012; G06T 2207/20081; G06T 2207/20084; G06T 2207/30004;
(Continued)

(56) References Cited

U.S. PATENT DOCUMENTS

| | | | |
|---|---|---|---|
| 8,189,866 B1 * | 5/2012 | Gu ......................... | G06V 40/20 348/169 |
| 2003/0058111 A1 * | 3/2003 | Lee .................. | G08B 13/19641 348/E7.086 |

(Continued)

OTHER PUBLICATIONS

Abhinav Gupta et al., Visual Features for Context-Aware Speech Recognition, 5 pages and 3 figures, Dec. 2017, 2017 IEEE International Conference on Acoustics, Speech and Signal Processing (ICASSP).

(Continued)

*Primary Examiner* — Van D Huynh
(74) *Attorney, Agent, or Firm* — AEON Law, PLLC; Adam L. K. Philipp; David V. H. Cohen

(57) ABSTRACT

There is provided a device configured to transcribe an appearance of a human being, said device comprising a common housing holding an image capturing sensor, a computing device comprising a data processor, and a computer program product comprising a first machine learning model trained for detecting and labeling human beings, a second machine learning model trained for detecting appearances of human beings and a transcription module to transcribe the detected appearances of human beings to text.

12 Claims, 8 Drawing Sheets

(51) Int. Cl.
*G16H 30/20* (2018.01)
*G16H 30/40* (2018.01)

(52) U.S. Cl.
CPC .............. *G06T 2207/20081* (2013.01); *G06T 2207/20084* (2013.01); *G06T 2207/30004* (2013.01); *G06T 2207/30196* (2013.01)

(58) Field of Classification Search
CPC .......... G06T 2207/30196; G16H 10/60; G16H 30/20; G16H 30/40; G06Q 10/10
USPC .......................................................... 382/128
See application file for complete search history.

(56) References Cited

U.S. PATENT DOCUMENTS

| | | | | |
|---|---|---|---|---|
| 2010/0303303 | A1* | 12/2010 | Shen | G06V 40/20 382/107 |
| 2011/0276396 | A1* | 11/2011 | Rathod | G06Q 20/10 707/706 |
| 2014/0247343 | A1* | 9/2014 | Chen | H04N 5/272 348/135 |
| 2017/0064363 | A1* | 3/2017 | Wexler | G06V 40/20 |
| 2018/0197624 | A1* | 7/2018 | Robaina | G06F 3/012 |
| 2018/0303397 | A1* | 10/2018 | Krupat | G16H 50/20 |
| 2018/0308565 | A1* | 10/2018 | Pinter | G06N 20/00 |
| 2018/0315200 | A1* | 11/2018 | Davydov | G10L 15/26 |

OTHER PUBLICATIONS

Bin Xiao et al., Simple Baselines for Human Pose Estimation and Tracking, Apr. 2018 Accepted by ECCV 2018.
Yilun Chen et al., Cascaded Pyramid Network for Multi-Person Pose Estimation, Aug. 18, 2018, 10 pages, accepted to CVPR 2018.
PCT/EP2020/058034 international search report dated Apr. 5, 2020.
PCT/EP2020/058034 Written Opinion dated May 8, 2020.

* cited by examiner

MEDICAL DEVICE FOR TRANSCRIPTION OF APPEARANCES IN AN IMAGE TO TEXT WITH MACHINE LEARNING

FIELD OF THE INVENTION

The invention relates to a device, a system, a method and a computer program product for the detecting and transcribing of appearances in an image to text using artificial intelligence.

BACKGROUND OF THE INVENTION

Documentation is a requirement in just about every job. In healthcare, it has even become a vital part of each staff member's role. Documentation is often the sole point of communication between healthcare workers of changing shifts. This means that if no verbal conversation has taken place, the documented notes must be read by the incoming healthcare worker in order to understand where the patient stands in the care cycle. In the case that a documentation error, or lack of documentation altogether, leads to a medical error that threatens a patient's life, the charting (or lack thereof) protects the patient in a court of law.

Artificial intelligence (AI) is developing rapidly and AI applications are supporting or will support all industries including the aerospace industry, agriculture, chemical industry, computer industry, construction industry, defense industry, education industry, energy industry, entertainment industry, financial services industry, food industry, health care industry, hospitality industry, information industry, manufacturing, mass media, mining, telecommunication industry, transport industry, water industry and direct selling industry.

Computer vision or machine vision is an area of AI wherein machine learning can be used to classify or to categorize scenes in images of living beings and objects. Computer vision is also a science that tries to understand what can be seen and what is happening in an image or series of images such as a photo picture, a video or a live stream. To that extend, machine learning can be used. An image contains a scene reflecting people, animals and/or objects showing a pose and often executing an activity.

Machine hearing is an area of AI wherein machine learning can be used to classify or to categorize sounds of living beings and objects. The technology allows a machine to selectively focus in a specific sound against many other competing sounds and background noise. This particular ability is called "auditory scene analysis". Moreover, the technology enables the machine to segment several streams occurring at the same time. Many commonly used devices such as a smartphones, smart speakers, voice translators, and vehicle voice command systems make use of machine hearing.

Human-machine communication becomes more and more important. Machines (such as computers, smartphones, tablets and robots) are penetrating society rapidly.

In "Cascaded Pyramid Network for Multi-Person Pose Estimation", revision August 2018, by Yilun Chen et al. (https://arxiv.org/pdf/1711.07319.pdf) according to its abstract describes "The topic of multi-person pose estimation has been largely improved recently, especially with the development of convolutional neural network. However, there still exist a lot of challenging cases, such as occluded keypoints, invisible keypoints and complex background, which cannot be well addressed. In this paper, we present a novel network structure called Cascaded Pyramid Network (CPN) which targets to relieve the problem from these "hard" keypoints. More specifically, our algorithm includes two stages: GlobalNet and RefineNet. GlobalNet is a feature pyramid network which can successfully localize the "simple" keypoints like eyes and hands but may fail to precisely recognize the occluded or invisible keypoints. Our RefineNet tries explicitly handling the "hard" keypoints by integrating all levels of feature representations from the GlobalNet together with an online hard keypoint mining loss. In general, to address the multi-person pose estimation problem, a top-down pipeline is adopted to first generate a set of human bounding boxes based on a detector, followed by our CPN for keypoint localization in each human bounding box. Based on the proposed algorithm, we achieve state-of-art results on the COCO keypoint benchmark, with average precision at 73.0 on the COCO test-dev dataset and 72.1 on the COCO test-challenge dataset, which is a 19% relative improvement compared with 60.5 from the COCO 2016 keypoint challenge. Code (https://github.com/chenyilun95/tf-cpn) and the detection results are publicly available for further research."

In "Simple Baselines for Human Pose Estimation and Tracking", April 2018, by Bin Xiao et al. (https://arxiv.org/pdf/1804.06208.pdf) according to its abstract describes "There has been significant progress on pose estimation and increasing interests on pose tracking in recent years. At the same time, the overall algorithm and system complexity increases as well, making the algorithm analysis and comparison more difficult. This work provides simple and effective baseline methods. They are helpful for inspiring and evaluating new ideas for the field. State-of-the-art results are achieved on challenging benchmarks. The code will be available at https://github.com/leoxiaobin/pose.pytorch".

US20180315200, with title "Monitoring System", according to its abstract describes "A monitoring system includes sensors that monitor activity within a designated territory. The sensors including visual sensors that make video recordings. A local processing system located within or proximate to the designated territory receives signals from the sensors. The local processing system processes and analyzes the signals from the sensors to produce messages that describe activity within the designated territory as monitored by the sensors. The messages do not include audio, visual or other direct identifying information that directly reveal identity of persons within the designated territory. A monitoring station outside the designated territory receives the messages produced by the local processing system and makes the messages available to external observers."

US20180308565, with title "Automated transcription and documentation of tele-health encounters", according to its abstract describes "Automatically generating a structured medical note during a remote medical consultation using machine learning. A provider tele-presence device may receive audio from a medical provider. A medical documentation server may be coupled to the network. A machine learning network receives audio data from the provider tele-presence device, the machine learning network generating a structured medical note based on the received audio data, and wherein the structured medical note is stored in the medical documentation server in association with an identity of a patient."

In "Visual Features for Context-Aware Speech Recognition", December 2017, by Abhinav Gupta et al. (https://arxiv.org/pdf/1712.00489.pdf) according to its abstract describes "Automatic transcriptions of consumer-generated multi-media content such as "Youtube" videos still exhibit high word error rates. Such data typically occupies a very broad domain, has been recorded in challenging conditions, with cheap hardware and a focus on the visual modality, and may have been post-processed or edited. In this paper, we extend our earlier work on adapting the acoustic model of a DNN-based speech recognition system to an RNN language model and show how both can be adapted to the objects and scenes that can be automatically detected in the video. We are working on a corpus of "how-to" videos from the web, and the idea is that an object that can be seen ("car"), or a scene that is being detected ("kitchen") can be used to condition both models on the "context" of the recording, thereby reducing perplexity and improving transcription. We achieve good improvements in both cases and compare and analyze the respective reductions in word error rate. We expect that our results can be used for any type of speech processing in which "context" information is available, for example in robotics, man-machine interaction, or when indexing large audio-visual archives, and should ultimately help to bring together the "video-to-text" and "speech-to-text" communities."

US20180197624, with title "Medical assistant", according to its abstract describes "A wearable device can present virtual content to the wearer for many applications in a healthcare setting. The wearer may be a patient or a healthcare provider (HCP). Such applications can include, but are not limited to, access, display, and modification of patient medical records and sharing patient medical records among authorized HCPs."

US20110276396, with title "System and method for dynamically monitoring, recording, processing, attaching dynamic, contextual and accessible active links and presenting of physical or digital activities, actions, locations, logs, life stream, behavior and status", according to its abstract describes "A system and method for dynamically monitoring, tracking, storing, processing & presenting physical or digital activities, actions, locations, behavior & status with dynamically attached active links is described. A method includes system, method, protocol, service, platform, and framework for dynamically monitoring, tracking, storing, determining, & processing user(s)' or any types of entities' physical or digital filtered activities, actions, interactions, responses, events, transactions, life stream, locations, behavior, movement, environment, status, states & conditions from one or more filtered sources and dynamically presenting said action or activity or status or log item(s) with dynamically attached active links to determined receivers, wherein said active links enables user to access action item specific functionalities including any types of application, service, accessing, processing functionalities, take one or more actions on action item, communicate, collaborate, participate, provide services & responses, workflow and any types of application, service functionalities."

US20100303303, with title "Methods for recognizing pose and action of articulated objects with collection of planes in motion", according to its abstract describes "The invention comprises an improved system, method, and computer-readable instructions for recognizing pose and action of articulated objects with collection of planes in motion. The method starts with a video sequence and a database of reference sequences corresponding to different known actions. The method identifies the sequence from the reference sequences such that the subject in performs the closest action to that observed. The method compares actions by comparing pose transitions. The cross-homography invariant may be used for view-invariant recognition of human body pose transition and actions."

U.S. Pat. No. 8,189,866, with title "Human-action recognition in images and videos", according to its abstract describes "The present disclosure includes, among other things, systems, methods and program products applying a plurality of low-level feature detectors to an image where each low-level feature detector produces a respective low-level feature vector that represents a detection result. The low-level feature vectors are provided to a plurality of higher-level feature detectors where each higher-level feature detector produces a respective higher-level feature vector that represents a detection result based on a distribution of features in one or more of the low-level feature vectors. The higher-level feature vectors are then provided to a classifier in order to classify a human-action in the image."

US20030058111, with title "Computer vision based elderly care monitoring system", according to its abstract describes "A method for monitoring a person of interest in a scene, the method comprising: capturing image data of the scene; detecting and tracking the person of interest in the image data; analyzing features of the person of interest; and detecting at least one of an event and behavior associated with the detected person of interest based on the features; and informing a third party of the at least one detected events and behavior."

US2018/303397 according to its abstract describes: "Techniques are described for image analysis and representation for emotional metric threshold generation. A client device is used to collect image data of a user interacting with a media presentation, where the image data includes facial images of the user. One or more processors are used to analyze the image data to extract emotional content of the facial images. One or more emotional intensity metrics are determined based on the emotional content. The one or more emotional intensity metrics are stored into a digital storage component. The one or more emotional intensity metrics, obtained from the digital storage component, are coalesced into a summary emotional intensity metric. The summary emotional intensity metric is represented."

SUMMARY OF THE INVENTION

Documentation is often a time-consuming task for professionals. Furthermore, noting an observation often involves documenting a subjective interpretation of the author. Since the reader of documentation will have his own subjective interpretation, there is often a discrepancy between what has been observed and what has been understood from the documentation.

The current invention overcomes the aforementioned deficits and allows to create documentation in an objective and verifiable way in order to limit errors made by a faulty interpretation of documentation.

Notably in the (health) care industry the current invention will have many advantages including, but not limited to: saving lives, better treatment of patients, better care for elderly, more reliable clinical trials and saving tremendous costs. The invention allows direct cost savings since care workers will spend less time on documentation. The invention allows indirect cost savings since better documentation will result in less errors. Errors in health(care) cannot only result in fatalities but can also result in very costly legal cases.

In addition, the current invention can support secret labeling of people that are being documented and/whilst preserving their anonymity.

To that end, there is provided a device configured to transcribe an appearance of a living being, said device comprising a common housing holding:
- an image capturing sensor;
- a computing device comprising a data processor, and
- a computer program product comprising:
  - a first machine learning model trained for detecting and labeling living beings;
  - a second machine learning model trained for detecting appearances of living beings;
  - a transcription module to transcribe the detected appearances of living beings to text, wherein said computer program product when running on said data processor:
- receives at least one image from said image capturing sensor;
- analyzes said at least one image, the analyzing comprises:
  - subjecting said at least one image to said first machine learning model;
  - detecting presence of a living being in said at least one image;
  - labeling the detected living being in said at least one image using a label;
  - subjecting at least a part of said at least one image, said part of said at least one image comprising the labeled living being, to said second machine learning model, and
  - retrieving said appearance of said labeled living being from said second machine learning model;
- applies said transcription module to transcribe the retrieved appearance, of said labeled living being, to text, and
- outputs said text.

In particular, there is provided a medical device of claim 1.

An image capturing sensor in an embodiment is a device that can provide an image or a series of images or a time series of images, in particular a digital image or digital picture. Such a device can comprise a camera of a filming (motion picture) device. Examples are devices comprising a CCD or similar imaging elements. Other examples are devices comprising a microphone for digitalizing sound into a sound image. Further examples of image capturing sensors are a camera, a sonar, a RADAR, a laser, LIDAR and an infrared camera. As such, these devices are known to a skilled person.

An image or a series of images or a time series of images result from said image capturing sensor or multiple devices of said image capturing sensor.

An appearance is in particular defined as a pose, an action or an activity of a living being An appearance in an embodiment expresses body language of a living being.

A living being is in particular defined as an animal or a human.

A subject can be living being, i.e. an animal or a person, or an object. A physical product is an example of an object, as is a car, a statue or a house.

A pose is the position and orientation of a subject. For humans and vertebrates with limbs, pose is defining the position of a body, limbs and head, in particular with respect to one another. The pose of living beings can be detected by articulated body pose estimation.

An action is in particular defined as a sequence of poses and is a movement of a subject having trajectory.

An activity in an embodiment is a series of actions.

Body language of a living being is best understood when taking into account the normal, i.e., a baseline body language.

Typically, body language is an involuntary and unconscious phenomenon that adds to the process of communication.

Body language comprises of movements and postures through which attitudes and feelings are communicated, such as "his intent was clearly expressed in his body language". In an embodiment, body language consists of these movements and postures.

Nonverbal communication can be by means of facial expressions, eye behavior, gestures, posture, and the like, and are often thought to be or supposed to be involuntary.

Body language is a type of nonverbal communication in which physical behavior, as opposed to words, is used to express or convey information. Such behavior includes body posture, gestures, touch, breath, facial expressions, eye expression, mouth expression, the use of space and appearance.

Body language comprises touching and how it is used in communication, also referred to as haptic communication. As such, handshakes, holding hands, back slapping, high fives, brushing up against someone or patting someone, this all has meaning in the context of communication.

Body language also comprises spatial relationships between living beings, which is also known as "proxemics". Introduced by Edward T. Hall in 1966, proxemics is the study of measurable distances between people as they interact with one another.

Body language further comprises breathing. Patterns of breathing and the context wherein breathing is evaluated are indicative for the mood and state of mind of humans and in general living beings. As such, deep breathing can indicate a relaxed mood and shallow, excessive rapid breathing as being in a more anxious, nervous or stressed state of mind.

The baseline body language of a living being is the body language the living being is expected to show under normal circumstances, in everyday life. Everyday life comprises the ways in which living beings typically act, move, touch, breath, look, speak, think, and feel on a daily basis. Everyday life may be described as routine, natural, habitual, or normal.

The body language message is derived from an amount of deviation of body language of a living being from its baseline body language.

Adapting an AI system results in an AI system that is able to recognize body language that expresses a body language message. Adapting an AI system may comprise calibrating an AI system with a baseline body language.

A baseline body language can be set on a group level or on an individual level. On the group level, in an embodiment the body language system determines the common baseline body language for a group of living beings sharing a common aspect that is typical for the group.

In an embodiment, the device is configured to transcribe said appearance of at least one living being within a plurality of living beings, wherein said analyzing comprises:
- detecting presence of said plurality of living beings in said at least one image;
- labeling said at least one living being within the detected plurality of living beings in said at least one image using a label;
- retrieving at least a part of said at least one image, said part of said at least one image comprising the labeled at least one living being within said detected plurality of living beings, resulting in at least one labeled image;

subjecting said at least one labeled image to said second machine learning model, and retrieving said appearance of said labeled at least one living being within said detected plurality of living beings from said second machine learning model.

In an embodiment, the device is configured to transcribe multiple appearances of said labeled living being, and said computer program product when running on said data processor:

receives multiple images from said image capturing sensor;

analyzes said multiple images, the analyzing comprises:

subjecting said multiple images to said first machine learning model;

detecting presence of said living being in a first image of said multiple images;

labeling the detected living being in said first image of said multiple images with said label;

retrieving at least a part of said first image of said multiple images, said part of said first image of said multiple images comprising the labeled living, resulting in a labeled first image;

detecting presence of said labeled living being in every further image of said multiple images;

labeling said detected living being in every further image of said multiple images with said label;

retrieving at least a part of said every further image of said multiple images, said part of said every further image of said multiple images comprising said labeled living, resulting in a labeled set of further images;

subjecting said labeled first image and said labeled set of further images to said second machine learning model, and retrieving said multiple appearances of said labeled living being from said second machine learning model;

applies said transcription module to transcribe the retrieved multiple appearances, of said labeled living being, to text, and outputs said text.

In an embodiment, the analyzing comprises:

subjecting a first image of said multiple images to said first machine learning model;

detecting presence of said living being in said first image of said multiple images;

labeling the detected living being in said first image of said multiple images with said label;

retrieving at least a part of said first image of said multiple images, said part of said first image of said multiple images comprising the labeled living, resulting in a labeled first image;

subjecting a further image of said multiple images to said first machine learning model;

detecting presence of said labeled living being in said further image of said multiple images;

labeling said detected living being in said further image of said multiple images with said label;

retrieving at least a part of said further image of said multiple images, said part of said further image of said multiple images comprising said labeled living, resulting in a labeled further image;

subjecting said labeled first image and said labeled further image to said second machine learning model, and retrieving said multiple appearances of said labeled living being from said second machine learning model.

In an embodiment, the device is configured to transcribe said appearance of each living being within a plurality of living beings, wherein said analyzing comprises:

a) detecting presence of a plurality of living beings in said at least one image;

b) labeling the detected plurality of living beings in said at least one image using a label for each detected living being;

c) retrieving at least one of the labeled living beings, resulting in a set of retrieved living beings;

d) subjecting at least a part of said at least one image, said part of said at least one image comprising at least one being of said set of retrieved living beings, to said second machine learning model, e) retrieving said appearance of said labeled living beings in said set of retrieved living beings from said second machine learning model, and f) repeating said c), d) and e) until said appearance of each living being within a plurality of living beings is retrieved, and wherein said computer program product when running on said data processor:

applies said transcription module to transcribe the retrieved appearances of said each living being within a plurality of livings beings to text, and outputs said text.

In an embodiment, the second machine learning model comprising:

a first deep neural network which captures the skeleton data of said living being in said at least a part of said at least one image, said first deep neural network using said at least a part of said at least one image as an input and outputs said skeleton data;

a second deep neural network which captures a first appearance of said living being, said second deep neural network using said skeleton data from said first deep neural network as an input and outputs said first appearance in first appearance data;

a third deep neural network which captures a second appearance of said living being in said at least a part of said at least one image, said third deep neural network using said at least a part of said at least one image as an input and outputs said second appearance in second appearance data, and a fourth deep neural network which captures a third appearance of said living being using said first and second appearance data as an input and outputs third appearance data, said third appearance data comprising a prediction of probabilities of said appearance.

In an embodiment, of the device:

said skeleton data comprises a k-dimensional vector;

said first appearance data comprises an n-dimensional first appearance vector;

said second appearance data comprises an m-dimensional second appearance vector, and said third appearance data comprises a p-dimensional third appearance vector, and wherein said second machine learning model further comprises:

a concatenation module which concatenate said m-dimensional second appearance vector and said n-dimensional first appearance vector into a (m+n)-dimensional intermediate vector.

In an embodiment, the computer program product receives multiple images providing a time series of images, inputs said multiple images in said second machine learning model providing a series of said third appearance data, concatenates said series of third appearance data and provides the concatenated output as input for a further deep neural network to predict probabilities of each appearances of the labelled living being present in said time series of images. This allows analysing more complex appearances, or may add more reliability.

In an embodiment, the multiple images comprise a time base, in an embodiment said multiple images comprise a part of a video recording or a series of time-laps images.

In an embodiment, the multiple images comprise a real-time processed video recording.

In an embodiment, the appearance comprises a pose.

In an embodiment, the appearances comprises a series of poses or a change of poses, said series of poses or change of poses defining at least one action.

In an embodiment, the transcription to text in said transcription module involves creating a medical record.

There is further provided a computer program product for running on a computing device of a device according to any one of the preceding claims, and when running on said data processor:
  receives at least one image from said image capturing sensor;
  analyzes said at least one image, the analyzing comprises:
  subjecting said at least one image to said first machine learning model;
  detecting presence of a living being in said at least one image;
  labeling the detected living being in said at least one image using a label;
  subjecting at least a part of said at least one image, said part of said at least one image comprising the labeled living being, to said second machine learning model;
  retrieving said appearance of said labeled living being from said second machine learning model;
  applies said transcription module to transcribe the retrieved appearance of said labeled living being to text, and
  outputs said text.

A computing device in an embodiment comprises one or more data processors. In an embodiment, it comprises a machine for automatically executing calculations or instructions. Examples (non-limiting) of computing device are a PC, a server, a cloud server, a locally distributed server environment, a computer cloud environment or any circuitry for performing particular functions in an electronic device.

A computing device may output a confidence value associated with one or more of the appearance categories.

To that end, there is provided a method for categorizing an appearance of a living being in a scene, comprising:
a computing device receiving a plurality of data points corresponding to said scene; the computing device determining at least one subsets of data points from said plurality of data points, wherein said at least one subsets of data points comprises said living being, said computing device categorizing said appearance in said sub-scene, said computing device transcribes said appearance to text and output said text.

In some embodiments, once the computing device determines a categorization for the one or more subsets of data points, the computing device may store a given label associated with the determined category for the plurality of data points. The plurality of data points may then become part of the training data which may be used for future determinations of appearances.

A computing device may identify patterns using the machine learning algorithm to optimize appearance detection, and/or scene detection in general. For instance, the machine learning algorithm may indicate that medical scenes comprise common characteristics, these characteristics may be a possible feature vector and utilized by the computing device (e.g. by the machine learning algorithm) to identify for instance a scene wherein a patient is being examined by a doctor.

There is provided an AI system comprising a computing device running the computer program product.

There is further provided an apparatus comprising the AI system, wherein said scene comprises a representation of a surrounding of said apparatus comprising said appearance, said AI system providing instructions to adjust at least one physical parameter of said apparatus based upon said categorizing of said appearance. Such a physical parameter comprises one of speed, direction, pose, position, and orientation in a space.

In an embodiment, such an apparatus comprises an image capturing sensor described above.

There is further provided a monitoring system comprising the AI system, wherein said scene comprises a representation of a surrounding of said monitoring system comprising said appearance, said AI system providing a signal based upon said transcription of text. In an embodiment, a signal comprises a notification, a control signal, a text message, an electromagnetic signal and an optical signal.

In an embodiment, there is provided a surveillance system comprising the monitoring system described above.

A scene can be defined as a view of a place of an occurrence or action comprising at least one subject.

In an embodiment, the scene is an indoor scene.

In an embodiment, the scene is an outdoor scene.

In an embodiment, the scene comprises a series of subsequent poses defining said action. In an embodiment, a scene is recorded in part of a video.

In order to detect and localize a subject in a scene from a captured image, in an embodiment use is made of a method to detect subjects. Such a method will use machine learning techniques (mainly deep learning) to design and train a model which detects subjects given an input of a visual representation, e.g. an RGB image, as the system perceives. The model is trained on a large amount of annotated data; it comprises images with and without subjects and locations of the subjects are annotated.

In the case of deep learning, a detection framework such as Faster-RCNN, SSD, R-FCN, Mask-RCNN, or one of their derivatives can be used. A base model structure can be VGG, AlexNet, ResNet, GoogLeNet, adapted from the previous, or a new one. A model can be initialized with weights and trained similar tasks to improve and speedup the training Optimizing the weights of a model, in case of deep learning, can be done with the help of deep learning frameworks such as Tensorflow, Caffe, or MXNET. To train a model, optimization methods such as Adam or RMSProp can be used. Classification loss functions such Hinge Loss or Softmax Loss can be used. Other approaches which utilize handcrafted features (such as LBP, SIFT, or HOG) and conventional classification methods (such as SVM or Random Forest) can be used.

In order to detect and localize a living being in a scene from a retrieved image an embodiment uses a method to detect living beings. Such a method will use machine learning techniques (mainly deep learning) to design and train a model which detects living beings given an input of a visual representation, e.g. an RGB image, as the system perceives. The model is trained on a large amount of annotated data; it comprises images with and without living beings and locations of the living beings are annotated.

To detect bodily features, the system in an embodiment can determine key points on the body (e.g. hands, legs, shoulders, knees, etc.) of a living being.

To detect the key points on the body of a living being, in an embodiment the system comprises a model that is designed and trained for this detection. The training data to train the model comprises an annotation of various key points locations. When a new image is presented, the model allows identification of the locations of such key points. To this end, the system can utilize existing key point detection approaches such as MaskRCNN or CMU Part Affinity Fields. The training procedure and data can be customized to best match the context of the content of the retrieved images. Such context may comprise an indoor context (like a doctor's office, home, a shop, an office, a station, an airport, a hospital, a theatre, a cinema etc.) or an outdoor context (like a beach, a field, a street, a square, a park etc.) wherein there are changing lighting conditions.

For example, a pretrained deep neural network (DNN) on ImageNet, e.g. VGGNet, AlexNet, ResNet, Inception and Xception, can be adapted by taking the convolution layers from these pretrained DNN networks, and on top of them adding new layers specially designed for scene recognition comprising one or more display devices, and train the network as described for the model. Additional new layers could comprise specially designed layers for action and pose recognition. All the aforementioned layers (scene recognition, pose and action recognition, body language recognition) can be trained independently (along with/without the pre-trained conventional layers) or trained jointly in a multi-task fashion.

In order to increase accuracy of a deep neural network (DNN) resulting in more reliable classifications, there is further provided a method for categorizing an appearance of a living being with a machine learning model comprising:
  a first deep neural network which captures skeleton data of said living being in at least a part of at least one image, said first deep neural network using said at least a part of said at least one image as an input and outputs said skeleton data;
  a second deep neural network which captures a first appearance of said living being, said second deep neural network using said skeleton data from said first deep neural network as an input and outputs said first appearance in first appearance data;
  a third deep neural network which captures a second appearance of said living being in said at least a part of said at least one image, said third deep neural network using said at least a part of said at least one image as an input and outputs said second appearance in second appearance data, and
  a fourth deep neural network which captures a third appearance of said living being using said first and second appearance data as an input and outputs third appearance data, said third appearance data comprising a prediction of probabilities of said appearance.

In an embodiment of this previous method:
said skeleton data comprises a k-dimensional vector;
said first appearance data comprises an n-dimensional first appearance vector;
said second appearance data comprises an m-dimensional second appearance vector, and
said third appearance data comprises a p-dimensional third appearance vector, and wherein said second machine learning model further comprises:
  a concatenation module which concatenate said m-dimensional second appearance vector and said n-dimensional first appearance vector into a (m+n)-dimensional intermediate vector.

In an embodiment thereof and/or of the previous method, multiple images providing a time series of images are input in said machine learning model resulting in a series of outputs, and wherein said series of outputs of said machine learning model are concatenated as input for a further deep neural network to predict probabilities of each appearance of the living being present in the time series of images.

In this way, appearances of one or more living beings can be determined even better using time laps.

The multiple images can be processed sequentially. In an embodiment, the multiple images are processed parallel or semi-parallel. This allows near-real time of even real time processing.

Categorization may involve identifying to which of a set of categories (e.g. normal pose or awkward pose and/or allowed action or prohibited action and/or normal condition scene or emergency scene and/or ordinary object or out-of-the-ordinary object) a new captured scene may belong, on the basis of a set of training data with known categories, such as the aforementioned categories. Categorization of the one or more subsets of data points associated with a captured scene may be performed using one or more machine learning algorithms and statistical classification algorithms. Example algorithms may include linear classifiers (e.g. Fisher's linear discriminant, logistic regression, naive Bayes, and perceptron), support vector machines (e.g. least squares support vector machines), clustering algorithms (e.g. k-means clustering), quadratic classifiers, multi-class classifiers, kernel estimation (e.g. k-nearest neighbor), boosting, decision trees (e.g. random forests), neural networks, Gene Expression Programming, Bayesian networks, hidden Markov models, binary classifiers, and learning vector quantization. Other example classification algorithms are also possible.

The process of categorization may involve the computing device determining, based on the output of the comparison of the one or more subsets with the one or more predetermined sets of scene types, a probability distribution (e.g. a Gaussian distribution) of possible scene types associated with the one or more subsets. Those skilled in the art will be aware that such a probability distribution may take the form of a discrete probability distribution, continuous probability distribution, and/or mixed continuous-discrete distributions. Other types of probability distributions are possible as well.

The term "statistically" when used herein, relates to dealing with the collection, analysis, interpretation, presentation, and organization of data. The analysis may be presented into visual formats like graphs, or other known graphical representations and/or tables.

The term "near real-time" or "nearly real-time" (NRT), in telecommunications and computing, refers to the time delay introduced, by automated data processing or network transmission, between the occurrence of an event and the use of the processed data, such as for display or feedback and control purposes. For example, a near-real-time display depicts an event or situation as it existed at the current time minus the processing time, as nearly the time of the live event.

The distinction between the terms "near real time" and "real time" is somewhat nebulous and must be defined for the situation at hand. The term implies that there are no significant delays. In many cases, processing described as "real-time" would be more accurately described as "near real-time". In fact, this may also be described as "functionally real-time".

Near real-time also refers to delayed real-time transmission of voice and video. It allows playing video images, in approximately real-time, without having to wait for an entire large video file to download. Incompatible databases can export/import to common flat files that the other database can import/export on a scheduled basis so that they can sync/share common data in "near real-time" with each other.

Real-time signal processing is necessary, but not sufficient in and of itself, for live signal processing such as what is required in live event support. Live audio digital signal processing requires both real-time operation and a sufficient limit to throughput delay so as to be tolerable to performers using stage monitors or in-ear monitors and not noticeable as lip sync error by the audience also directly watching the performers. Tolerable limits to latency for live, real-time processing is a subject of investigation and debate but is estimated to be between 6 and 20 milliseconds.

A real-time system has been described in Wikipedia as one which "controls an environment by receiving data, processing them, and returning the results sufficiently quickly to affect the environment at that time". The term "real-time" is also used in simulation to mean that the simulation's clock runs at the same speed as a real clock, and in process control and enterprise systems to mean "without significant delay".

The distinction between "near real-time" and "real-time" varies, and the delay is dependent on the type and speed of the transmission. The delay in near real-time is typically of the order of several seconds to several minutes.

Often, systems that are described or seen as "real-time" are functionally real-time.

Demography in general is the statistical study of populations, especially human beings (see Wikipedia). As a very general science, it relates to analyzing any kind of dynamic living population, i.e., one that changes over time or space. Demography encompasses the study of the size, structure, and distribution of these populations, and spatial or temporal changes in them in response to birth, migration, aging, and death.

Demographic analysis can cover whole societies or groups defined by criteria such as education, nationality, religion, and ethnicity.

Formal demography limits its object of study to the measurement of population processes, while the broader field of social demography or population studies also analyses the relationships between economic, social, cultural, and biological processes influencing a population.

The common variables that are gathered in demographic research include age, sex, income level, race, employment, marital state, occupation, religion, location, home ownership and level of education. Demographics make certain generalizations about groups to identify customers. Additional demographic factors include gathering data on preferences, hobbies, lifestyle and more.

A camera is defined in for instance Wikipedia as an optical instrument for recording or capturing images, which may be stored locally, transmitted to another location, or both. The images may be individual still photographs or sequences of images constituting videos or movies. The camera is a remote sensing device as it senses subjects without any contact. Current cameras are in general digital image recording devices. A camera in general works with the light of the visible spectrum or with other portions of the electromagnetic spectrum. A still camera is an optical device which creates a single image of an object or scene and records it on an electronic sensor. A movie camera or a video camera operates similarly to a still camera, except it records a series of static images in rapid succession, commonly at a rate of 24 frames per second.

There is further provided a medical system configured to transcribe an appearance of a human being, said medical system comprising:
   an image capturing sensor;
   a computing device comprising a data processor and a computer program product which when running on said data processor causes said computing device to:
   retrieve at least one image from said image capturing sensor;
   analyze said at least one image, the analyzing comprises:
   input said at least one image to a first machine learning model trained for detecting and labeling human beings in at least one image, said first machine learning model labeling the human being in said at least one image using a label;
   input at least a part of said at least one image with said labelled human being to a second machine learning model trained for detecting appearances of human beings in at least one image, said second machine learning model providing said appearance of said labeled human being as an output, and
   apply a transcription module to transcribe the retrieved appearance of said labeled human being to text and output said text, wherein said transcription module creates a medical record and outputs said text into said medical record.

The term "substantially" herein, such as in "substantially all emission" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of".

The term "functionally" will be understood by, and be clear to, a person skilled in the art. The term "substantially" as well as "functionally" may also include embodiments with "entirely", "completely", "all", etc. Hence, in embodiments the adjective functionally may also be removed. When used, for instance in "functionally parallel", a skilled person will understand that the adjective "functionally" includes the term substantially as explained above. Functionally in particular is to be understood to include a configuration of features that allows these features to function as if the adjective "functionally" was not present. The term "functionally" is intended to cover variations in the feature to which it refers, and which variations are such that in the functional use of the feature, possibly in combination with other features it relates to in the invention, that combination of features is able to operate or function. For instance, if an antenna is functionally coupled or functionally connected to a communication device, received electromagnetic signals that are receives by the antenna can be used by the communication device. The word "functionally" as for instance used in "functionally parallel" is used to cover exactly parallel, but also the embodiments that are covered by the word "substantially" explained above. For instance, "functionally parallel" relates to embodiments that in operation function as if the parts are for instance parallel.

This covers embodiments for which it is clear to a skilled person that it operates within its intended field of use as if it were parallel.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices or apparatus herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device or apparatus claims enumerating several means, several of these means may be embodied by one and the same item of hardware. The mere fact that certain measures are recited in mutually different dependent claims does not indicate that a combination of these measures cannot be used to advantage.

The invention further applies to an apparatus or device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which.

The drawings are not necessarily on scale.

DESCRIPTION OF PREFERRED EMBODIMENTS

The following detailed description describes various features and functions of the disclosed systems and methods with reference to the accompanying figures. In the figures, similar symbols identify similar components, unless context dictates otherwise.

Figure 1:
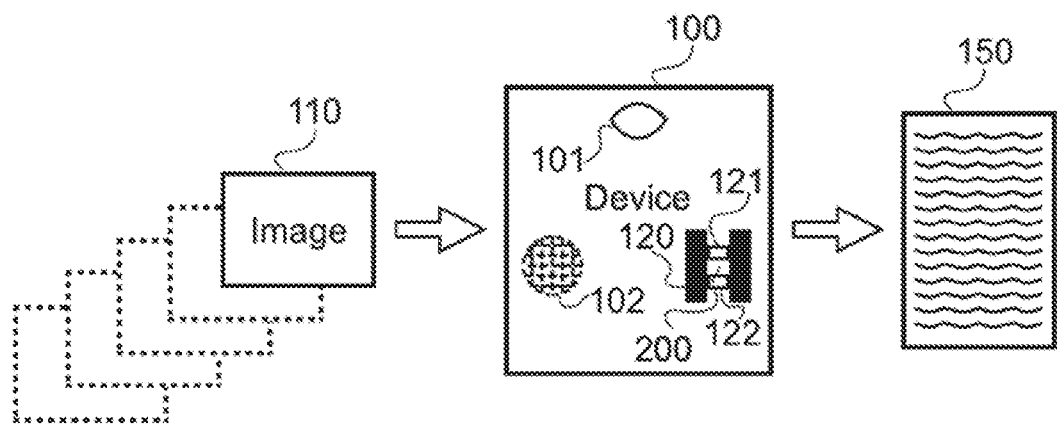
FIG. 1 depicts a simplified diagram of an embodiment of a device configured to transcribe an appearance of a living being to text.

FIG. 1 depicts a simplified diagram of an embodiment of a device 100 configured to transcribe an appearance of a living being. Device 100 has an image capturing sensor 101 for capturing at least one image 110 comprising an image of a living being, a computing device 120 comprising memory 122 and a data processor 121, and a computer program product 200 wherein the computer program product when running on the data processor executes a method 300 (FIG. 3) for transcribing an appearance of the living being to text 150 and for outputting the text 150.

The data processor 121 included in the computing device 120 may comprise one or more general-purpose processors and/or one or more special-purpose processors (e.g., image processor, digital signal processor, etc.). To the extent that the data processor 121 includes more than one processor, such processors could work separately or in combination.

The memory 122 may comprise one or more volatile and/or one or more non-volatile storage components, such as optical, magnetic, and/or organic storage, and the memory 122 may be integrated in whole or in part with the data processor 121. The memory 122 may contain the computer program product 200 (e.g., program logic) executable by the data processor 121 to execute various functions, including any of the functions or methods described herein.

In an embodiment, a device 100 has a microphone 102. Microphone 102 can provide a sound image that may enrich the information provided by an image capturing sensor. For instance, when a transcription text 150 is created for a medical SOAP (subjective, objective, assessment, and plan) note in order to document a patient's motor skills while the patient is coughing.

In a further embodiment, more than one image capturing sensor may be part of a device 100. For instance, the LIDAR device may be configured to provide to the computer program product 200 a cloud of point data representing subjects (e.g. living beings and objects), which have been hit by the laser. The points may be represented by the LIDAR device in terms of azimuth and elevation angles, in addition to range, which can be converted to (X, Y, Z) point data relative to a local coordinate frame attached to the LIDAR device. Additionally, the LIDAR device may be configured to provide to the computer program product 200 intensity values of the light or laser reflected off the subjects that may be indicative of a surface type of a given subject. Based on such information, the computer program product may be configured to identify the subject and parameters of the subject such as type of the subject, size, height, speed, whether the subject is a living being or a certain type object.

In a further embodiment of device 100, the device 100 outputs text 150 over a wireless and/or wired connection.

In a further and/or other embodiment of device 100, a text 150 is first encrypted and output to be stored on any type of computer readable medium or memory, for example, such as a storage device including a disk or hard drive. This allows to preserve the confidentially of text 150. Afterwards, the confidentiality of the text 150 could be lifted in case of for instance an alleged sexual harassment or any other event that would require (legal) investigation.

In examples, an installed embodiment of device 100 could monitor (public) places such as train/bus stations, airports, schools, prisons, universities, hospitals, elderly homes, theaters, arenas and outdoors spaces (streets and squares), in addition to factories, offices, shops, doctor/therapist practices, gyms, dressing rooms and lifts.

In an embodiment, there is provided a security device comprising the device 100, wherein said appearance comprises a pose, an action or body language expressing unauthorized behavior, in particular illegal behavior, from said living being. The device or method may thus provide a log message or an alarm message without need for storing images, and, in case of logging, without the need of storing information about appearances of no interest, i.e. authorized behavior, in particular legal behavior.

In a further embodiment, there is provided a security device comprising the device 100, wherein said appearance comprises a pose, an action or body language expressing aggression from said living being towards another living being present in said at least one image, in particular expressing sexual harassment.

In other examples, an installed embodiment of device 100 could monitor animals in a zoo or live stock at a farm.

Figure 2:
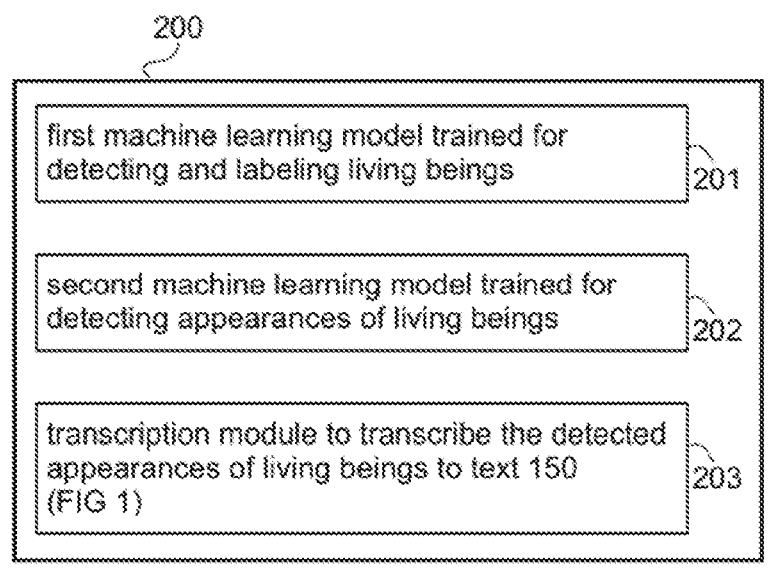
FIG. 2 depicts a simplified block diagram of a computer program product configured to transcribe an appearance of a living being to text.

FIG. 2 depicts a simplified block diagram of a computer program product 200 configured to transcribe an appearance of a living being to text 150 (FIG. 1), in accordance with an example embodiment. Components coupled to or included in the computer program product 200 may include a component 201, i.e. a first machine learning model trained for detecting and labeling living beings, and may include a component 202, i.e. a second machine learning model trained for detecting appearances of living beings, and may include a component 203, i.e. a transcription module to transcribe the detected appearances of living beings to text 150 (FIG. 1).

In other embodiments, the computer program product 200 may include more, fewer, or different systems, and each system may include more, fewer, or different components. Additionally, the systems and components shown may be combined or divided in any number of ways.

In an embodiment a component 201 takes as input the at least one image comprising a plurality of data points and labels a subset of the plurality of data points that corresponds to at least one living being.

In a further embodiment a component 201 takes as input the at least one image comprising a plurality of data points and labels multiple subsets of the plurality of data points that corresponds to a living being.

In an embodiment related to humans a component 202 detects when a human shows an activity corresponding to "washing hands", "brushing teeth", "taking a bath", "taking a shower", "washing cloths", "doing the dishes", "cleaning the room" or a combination thereof.

In a further embodiment related to humans a component 202 detects when a baby shows an activity corresponding to "turning on stomach", "turning on side" or a combination thereof.

In a further other embodiment related to humans a component 202 detects when a human shows an activity corresponding to "smoking".

In yet another embodiment related to humans a component 202 detects a "man-down" situation, wherein a human is laying on the floor and is likely to need help.

In an embodiment related to living beings a component 202 detects when a living being shows an activity corresponding to "drinking", "eating", "sleeping" or a combination thereof.

In a further embodiment related to living beings a component 202 detects when a living being shows body language corresponding to "aggressive behavior", "defensive behavior", "calm behavior", "nervous behavior", "anxious behavior", or a combination thereof.

In an embodiment, a device comprises a computer memory provided with a database holding a document format corresponding to one selected from SOAP (subjective, objective, assessment, and plan), OODA (Observe, orient, decide, act), and a combination thereof, and said transcription module retrieves a said document format and inserts said text in said retrieved document format.

In an embodiment configured for humans, there is provided a hygiene detector wherein said second machine learning model is trained for detecting an appearance comprising washing of hands, and when a human is detected without said appearance, then said output text indicates that no hand washing has taken place. In response of this, a discernible signal can be provided indicating that no hand washing has taken place. For instance, a light signal, a sound signal, of even a spoken text, for instance "please wash your hands" can be output.

In an embodiment configured for human babies, there is provided a "false position" detector wherein said second machine learning model is trained for detecting an appearance comprising a baby laying on its stomach or a baby laying on its side, and when a baby is detected with said appearance, then said output text indicates that said baby is in a false position. In response of this, a discernible signal can be provided indicating that a baby is in a false position. For instance, a light signal, a sound signal, of even a spoken text, for instance "alarm, parent assistance needed" can be output.

In an embodiment configured for humans, there is provided a smoking detector wherein said second machine learning model is trained for detecting an appearance comprising said living being smoking for instance a cigarette, and when a human is detected with said appearance, then said output text indicates smoking. In response of this, a discernible signal can be provided indicating that smoking takes place. For instance, a light signal, a sound signal, of even a spoken text, for instance "please do not smoke" can be output.

In an embodiment configured for humans, there is provided a "person down" detector wherein said second machine learning model is trained for detecting an appearance comprising a person is down, and when a person is detected with said appearance, then said output text indicates that said person is down. In response of this, a discernible signal can be provided indicating that a person is down. For instance, a light signal, a sound signal, of even a spoken text, for instance "alarm, medical assistance needed" can be output.

In an embodiment, a transcription module of component 203 just logs the detected appearances in text corresponding to the naming of appearance categories detected in component 202.

In a further embodiment, a component 203 transcribes the detected appearances to text according to natural spoken language.

In a further other embodiment, a component 203 transcribes the detected appearances to text according to a specialized language; such as generally used between experts in a certain profession (for instance experts in law, security, care, medical service or financial services)

A transcription module can for instance be implemented by linking appearance categories to preferred words and phrases for outputting. In addition, various specialized and open source software libraries are available for generating text in a preferred language. In an embodiment, the transcription module comprises a database holding words and text fragments, and in operation said transcription module selects text selected from said words and said text fragments and outputs selected text as said text.

Figure 3:
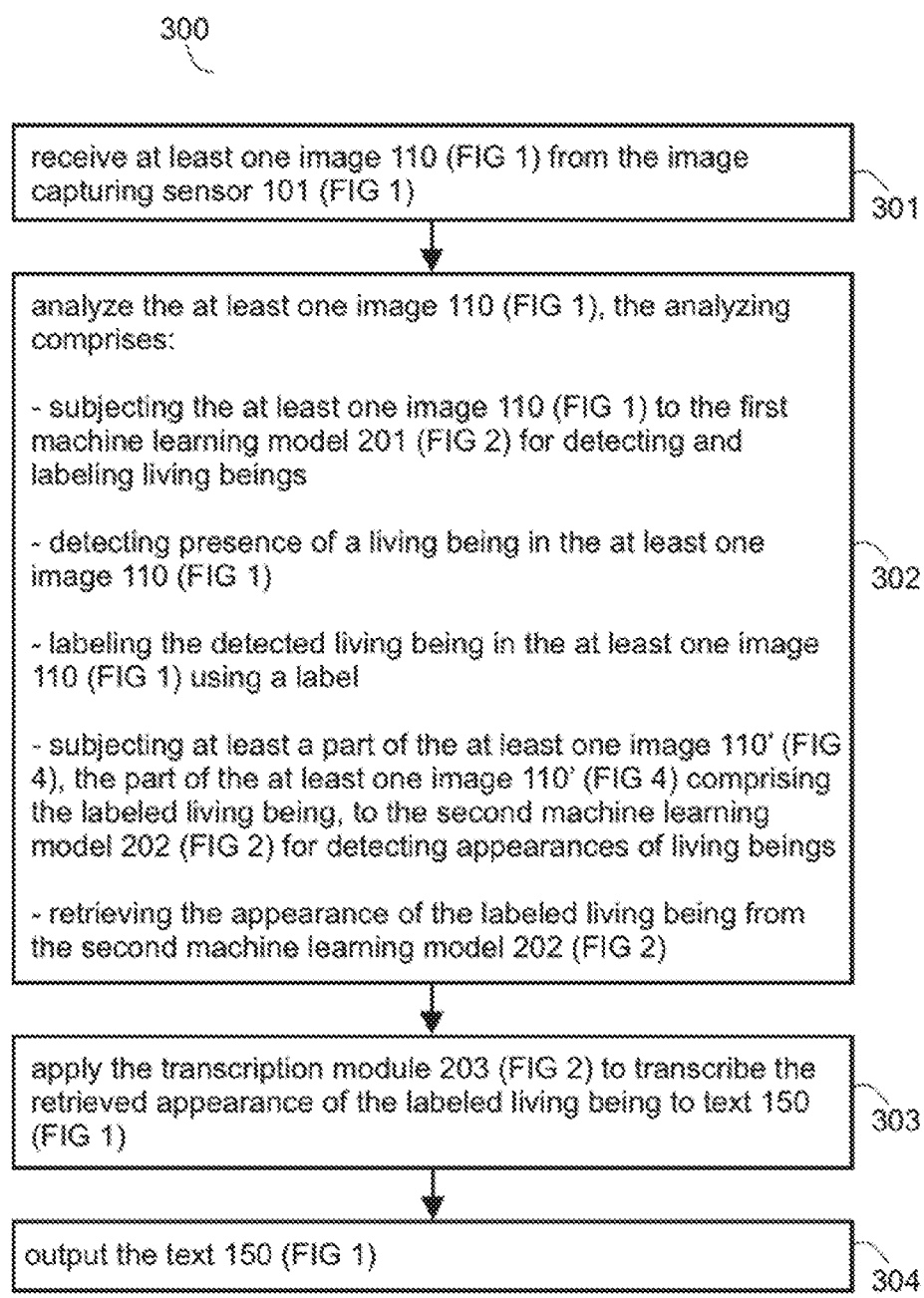
FIG. 3 depicts a flow chart of an example method for transcribing an appearance of a living being to text.

FIG. 3 depicts a flow chart of an example method 300 for transcribing an appearance of a living being to text 150 (FIG. 1). The method 300 may include one or more operations, functions, or actions as illustrated by one or more of blocks 301-304. Although the blocks are illustrated in a sequential order, these blocks may in some instances be performed in parallel. Also, the various blocks may be combined into fewer blocks, divided into additional blocks, and/or removed based upon the desired implementation.

In addition, for the method 300 and other processes and methods disclosed herein, the flow chart shows functionality and operation of one possible implementation of present embodiments. In this regard, each block may represent a module, a segment, or a portion of program code, which includes one or more instructions executable by data processor 121 (FIG. 1) for implementing specific logical functions or steps in the process. The computer program product 200 may be stored on any type of computer readable medium or memory, for example, such as a storage device including a disk or hard drive.

In addition, for the method 300 and other processes and methods disclosed herein, each block in FIG. 3 may represent circuitry that is wired to perform the specific logical functions in the process. For the sake of example, the method 300 shown in FIG. 3 will be described as implemented by an example computer program product such as the computer program product 200 (FIG. 2). The method 300 can also be described as implemented by a camera or computing device, as the computing device and the computer program product may be onboard the camera or may be off-board but in wired or wireless communication with the camera. Therefore, the terms "computer device", "computer program product" and "camera" can be interchangeable herein. It should be understood that other entities or combinations of entities can implement one or more steps of the example method 300.

At block 301, the method 300 includes: receive at least one image 110 (FIG. 1) from the image capturing sensor 101 (FIG. 1).

In an embodiment the at least one image (e.g. a plurality of data points) corresponds to the view of a camera.

In a further embodiment the at least one image corresponds to sounds (including noise) within a record sensibility of a microphone 102 (FIG. 1).

In a further other embodiment, the at least one image corresponds to LIDAR/RADAR-based information that may be indicative, for example, of dimensional parameters of a given subject, and may indicate whether the given subject is stationary or moving.

At block 302, the method 300 includes: analyze the at least one image 110 (FIG. 1), the analyzing comprises:

subjecting the at least one image 110 (FIG. 1) to the first machine learning model 201 (FIG. 2) for detecting and labeling living beings;

detecting presence of a living being in the at least one image 110 (FIG. 1);

labeling the detected living being in the at least one image 110 (FIG. 1) using a label;

subjecting at least a part of the at least one image 110' (FIG. 4), the part of the at least one image 110' (FIG. 4) comprising the labeled living being, to the second machine learning model 202 (FIG. 2) for detecting appearances of living beings;

retrieving the appearance of the labeled living being from the second machine learning model 202 (FIG. 2).

Although listed in a sequential order, these actions for the analyzing may in some instances be performed in parallel. Also, the various actions may be combined into fewer actions, divided into additional actions, and/or removed based upon the desired implementation.

At block 303, the method 300 includes: apply the transcription module 203 (FIG. 2) to transcribe the retrieved appearance of the labeled living being to text 150 (FIG. 1).

At block 304, the method 300 includes: output the text 150 (FIG. 1). The output of text 150 (FIG. 1) may be encrypted to preserve the confidentiality of its content.

Figure 4:
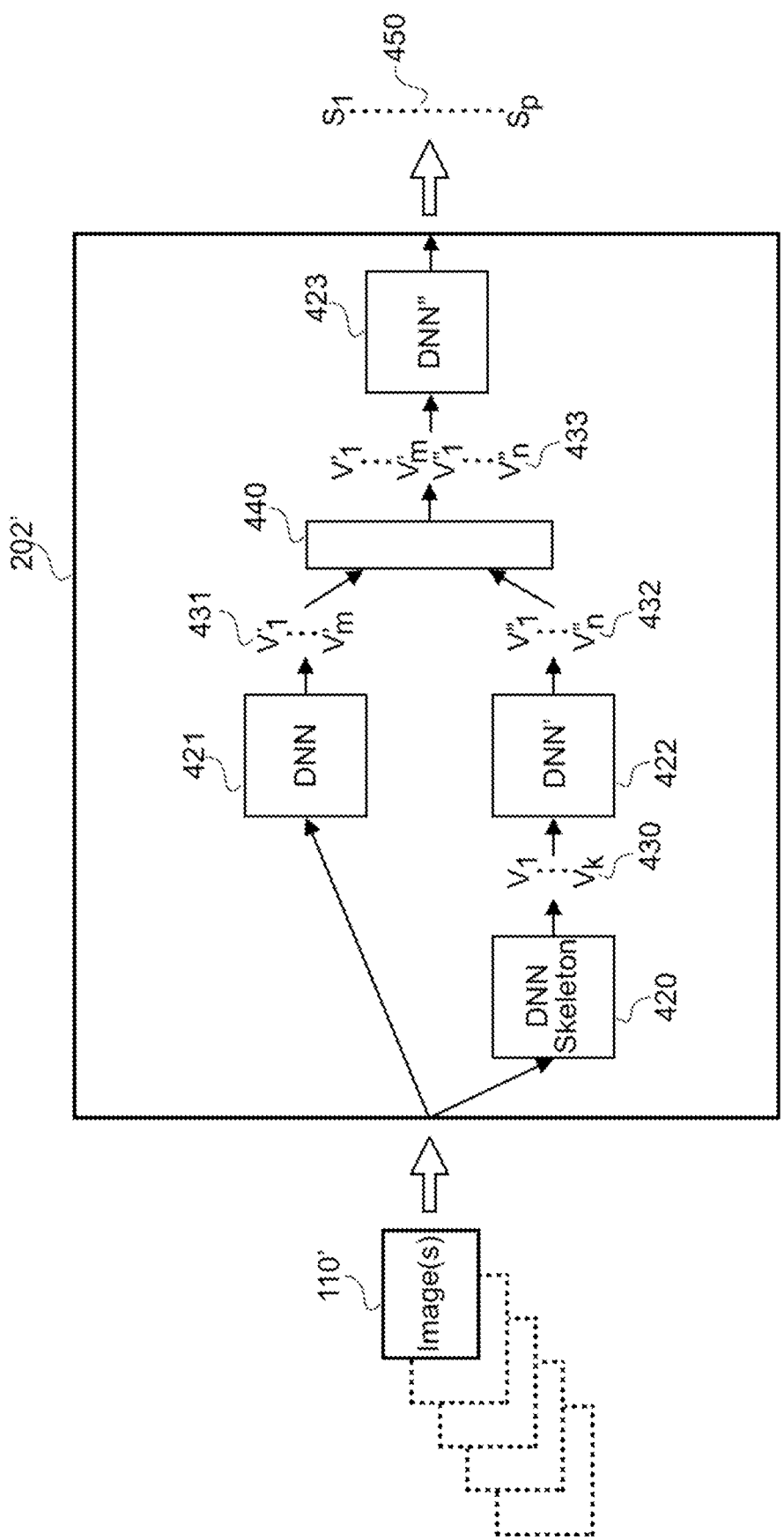
FIG. 4 schematically depicts an example embodiment of a machine learning model configured to detect appearances.

FIG. 4 schematically depicts an example embodiment of a machine learning model 202 (FIG. 2) configured to detect appearances, by a deep neural network (DNN) 202'.

The DNN 202' can be trained end-to-end. The DNN 202' detects appearances S of a labeled living being by categorizing p appearances S of the labeled living being from image 110' wherein image 110' is the at least a part of the at least one image 110 (FIG. 1) comprising a labeled living being.

The DNN 202' receives image 110' as input to predict probabilities 450 of each of p appearances S of the labeled living being present in image 110'. The DNN 202' is composed of multiple modules.

A first module is a DNN 420 that encodes the input image 110' into an k-dimensional vector representation 430 which captures skeleton-based information of the labeled living being. The skeleton-based information comprises a set of joint locations of the labeled living being.

A second module is a DNN 422 that encodes the skeleton-based information, from vector 430, into an n-dimensional vector representation 432 which captures first appearance-based information of the labeled living being.

A third module is a DNN 421 that encodes the input image 110' into an m-dimensional vector representation 431 which captures second appearance-based information of the labeled living being.

A fourth module is a concatenation layer 440 that concatenates the m-dimensional vector representation 431 and the n-dimensional vector representation 432 into a (m+n)-dimensional vector representation 433.

A fifth module is a DNN 423 that encodes the (m+n)-dimensional vector representation into a prediction of the probabilities 450 of each of p appearances S of the labeled living being present in image 110'.

In an embodiment, image 110' is a 2D image wherein the joint locations of the labeled living being are represented in (x,y)-coordinates.

In a further embodiment, image 110' is a 3D image wherein the joint locations of the labeled living being are represented in (x,y,z)-coordinates.

In further other embodiment, image 110' is a n-dimensional image wherein the joint locations of the labeled living being are represented in $(x_1, x_2, \ldots, x_n)$-coordinates.

In an embodiment DNN 421, DNN 422 and DNN 423 categorize the same set of appearance categories; such as a set of appearance categories comprising: standing, walking, sitting and laying.

In a further embodiment DNN 421, DNN 422 and DNN 423 categorize different sets of appearance categories. For instance DNN 421 categorizes a set of appearance categories comprising: active in various indoor/outdoor scenes and inactive in various indoor/outdoor scenes, and DNN 422 categorizes a set of appearance categories comprising: laying with various arm/leg positions, sitting with various arm/leg positions and standing with various arm/leg positions, while DNN 423 categorizes a set of appearance categories comprising: cooking, cleaning, washing hands, reading, phoning, walking, fishing, jogging, relaxing, mandown and sleeping.

In a further other embodiment DNN 421, DNN 422 and DNN 423 categorize partly different sets of appearance categories. For instance, DNN 421 and DNN 422 categorize a set of appearance categories comprising: laying with various arm/leg positions, sitting with various arm/leg positions and standing with various arm/leg positions, while DNN 423 categorizes a set of appearance categories comprising: standing, walking, sitting and laying.

In an embodiment, DNN 420 is a deep neural network such as a cascaded pyramid network (CPN) ["Cascaded Pyramid Network for Multi-Person Pose Estimation", April 2018, by Yilun Chen et al. (https://arxiv.org/pdf/1711.07319.pdf)].

In a further embodiment, DNN 420 is a deep neural network according to a deep neural network model such as proposed by the article "Simple Baselines for Human Pose Estimation and Tracking" [Simple Baselines for Human Pose Estimation and Tracking", April 2018, by Bin Xiao et al. (https://arxiv.org/pdf/1804.06208.pdf)].

In an embodiment, DNN 421 is a convolutional neural network such as AlexNet, ZFNet, GoogLeNet, VGGNet (e.g. VGG16 and VGG19) and ResNet (e.g. Resnet152 and ResNet50).

In an embodiment, DNN 422 is a deep neural network such as a multi-layer perceptron network.

In a further embodiment, DNN 422 is a deep neural network such as a recurrent neural network (RNN). An example of such a network is a long short-term memory (LSTM) network which treats 17 human joints as a sequence of 17 elements.

In a further other embodiment, DNN 422 is a deep neural network such as graph convolutional neural network (GCN).

In an embodiment, DNN 423 is a deep neural network such as a multi-layer perceptron network.

In an embodiment DNN 202' is be implement with the deep learning framework PyTorch.

In a further embodiment DNN 202' is be implement with the deep learning framework TensorFlow.

Figure 5:
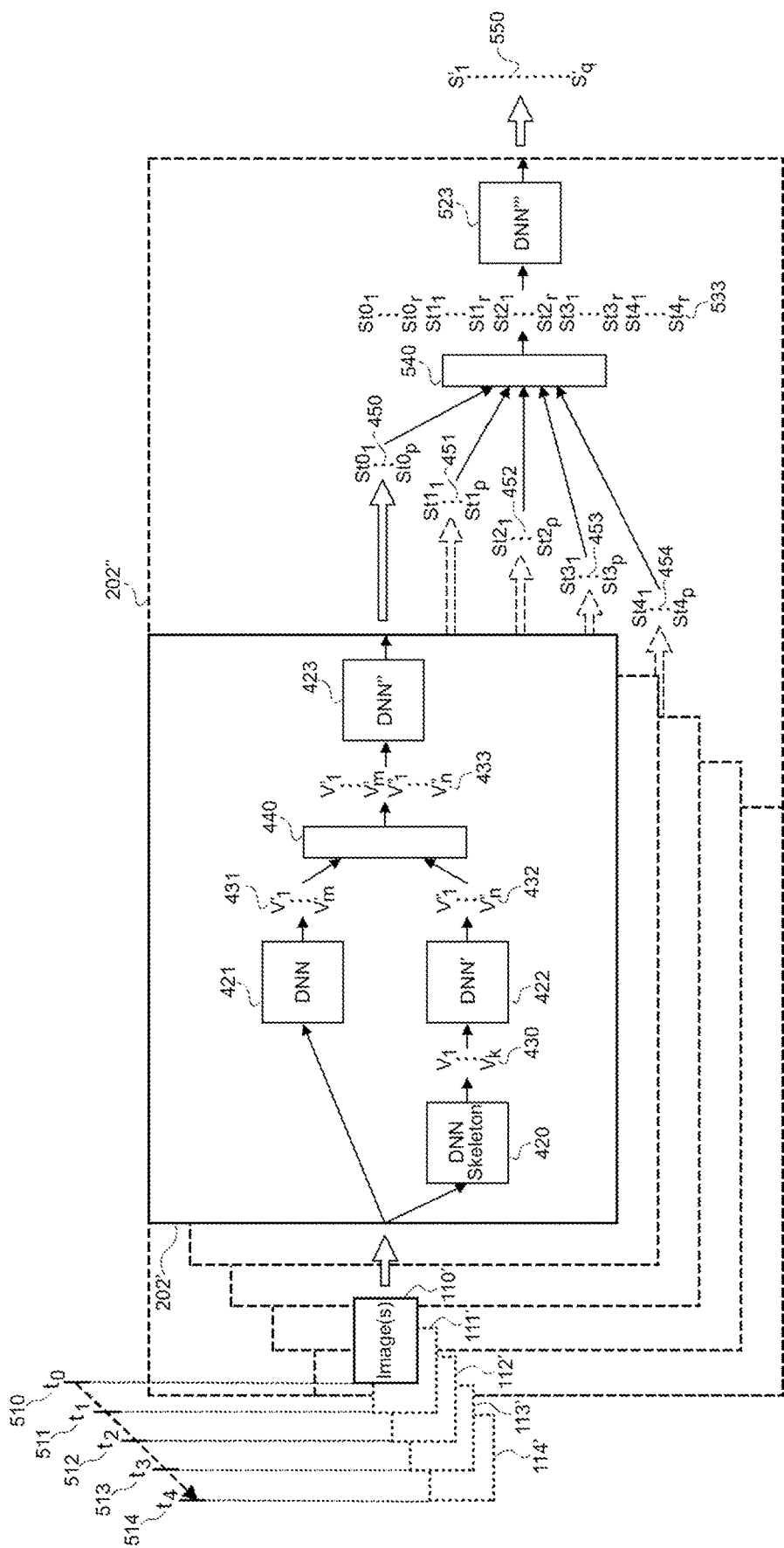
FIG. 5 schematically depicts an example embodiment of a machine learning model configured to detect appearances during a time interval.

FIG. 5 schematically depicts an example embodiment of a machine learning model 202 (FIG. 2) configured to detect appearances during a time interval, by a deep neural network (DNN) 202".

The DNN 202" can be trained end-to-end. The DNN 202" detects appearances S' of a labeled living being by categorizing q appearances S' of the labeled living being from multiple images 110', 111', 112', 113' and 114' captured at different times, respectively times 510, 511, 512, 513 and 514, and wherein each of the multiple images 110', 111', 112', 113' and 114' is the at least a part of the at least one image 110 (FIG. 1) comprising the labeled living being.

In an embodiment DNN 202' and DNN 202" categorize the same set of appearance categories; such as a set of appearance categories comprising: head bended, left/right arm stretched, left/right leg stretched, left/right hand rise, prayer pose, arms crossed and power pose.

In a further embodiment DNN 202' and DNN 202" categorize different sets of appearance categories. For instance, DNN 202' categorizes a set of appearance categories comprising: head bended yes/no, left/right arm stretched, left/right leg stretched, left/right hand rise, prayer pose, arms crossed and power pose, while DNN 202" categorizes a set of appearance categories comprising: nod yes/shake no, waving goodbye, stop sign, leg injury, defensive behavior and aggressive attitude.

Figure 6:
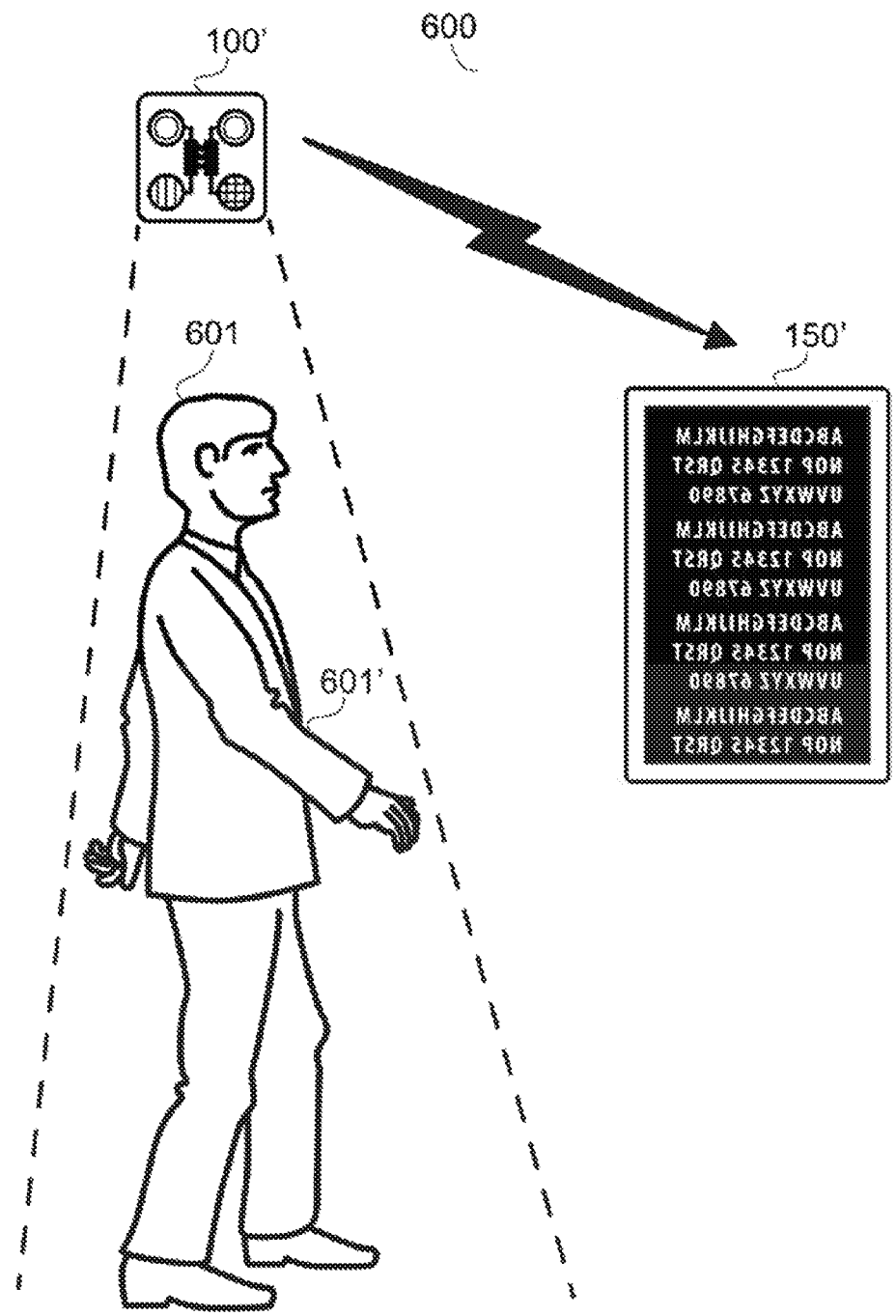
FIG. 6 depicts an example of a transcription of a person's appearance to text.

FIG. 6 depicts an example 600 of a transcription of a person's appearance 601' to text 150' by an example embodiment of a device 100'. The device 100' categorizes the appearance 601' of person 601 and transcribes the appearance 601' to text 150' and outputs the text 150'

In an example, the outputting of text 150' by an example embodiment of a device 100' implies storing a text 150' on any type of computer readable medium or memory, for example, such as a storage device including a disk or hard drive that is coupled to the device 100' by a wired or wireless connection.

In another example, the outputting of text 150' by an example embodiment of a device 100" implies sending out a notification, such as a text/SMS message, an email message, a chat message or any other readable message by a notification module configured to support a preferred message protocol. The notification module may either be integrated in a device 100' or be coupled to a device 100' by a wired or wireless connection.

Figure 7:
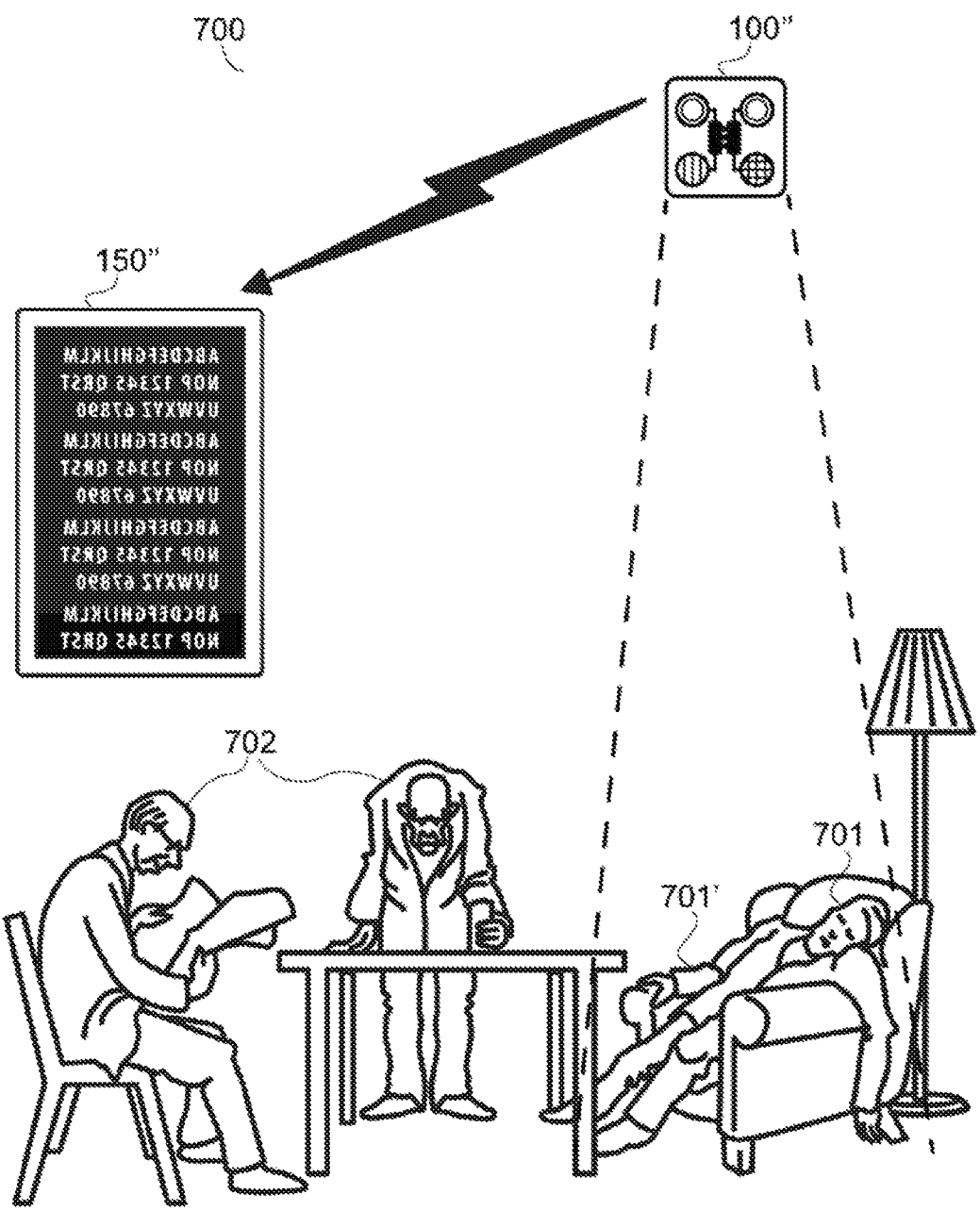
FIG. 7 depicts an example of a transcription of a person's appearance to text among others.

FIG. 7 depicts an example 700 of a transcription of a person's appearance 701' to text among others to text 150" by an example embodiment of a device 100". The device 100" tracks multiple persons (701 and 702) in an elderly home. In example 700, device 100" detects an awkward appearance of person 701 with appearance 701' while the appearances of others 702 seems normal. In this example device 100" transcribes the appearance 701' to text 150" and outputs the text 150".

In an example, the outputting of text 150" by an example embodiment of a device 100" implies storing a text 150" or sending out a notification as described before.

In another example, an example embodiment of a device 100" can assist with extensive diagnosing a mental or psychical condition of a person (e.g. a client, a patient or a criminal) during time intervals that attended observations wouldn't be possible. This allows to register 24/7 observations wherein image data is being transcribed to text. An embodiment as such would have multiple advantages compared to directly recording image data, such as:

- a transcription of observations in text format generally will take less data storage;
- a detection of appearances allows filtering and only storing of events comprising appearances of interest, saving additional data storage;
- a transcription to text hides explicit image footage and therefore protects the privacy of a person being observed, and
- a transcription to text enables hiding the identity of a person being observed by labeling a detected person with a secret label; such a secret label may be unknown to anybody and therefore fully anonymizing a detected person or such a secret label may be confidential and only known by authorized people (e.g. a treating doctor, a police officer, family member).

There is further provided a method for transcribing an appearance of each living being within or amongst a plurality of living beings in at least part of an image, comprising:

a) detecting presence of a plurality of living beings in said at least one image;

b) labeling the detected plurality of living beings in said at least one image using a label for each detected living being;

c) retrieving at least one of the labeled living beings, resulting in a set of retrieved living beings;

d) subjecting at least a part of said at least one image, said part of said at least one image comprising at least one being of said set of retrieved living beings, to said second machine learning model, e) retrieving said appearance of said labeled living beings in said set of retrieved living beings from said second machine learning model, and f) repeating said steps c), d) and e) until said appearance of each living being within a plurality of living beings is retrieved.

In an embodiment of this method, there is provided a computer program product which, when running on a data processor:

applies said transcription module to transcribe the retrieved appearances of said each living being within a plurality of livings beings to text, and outputs said text.

Figure 8A:
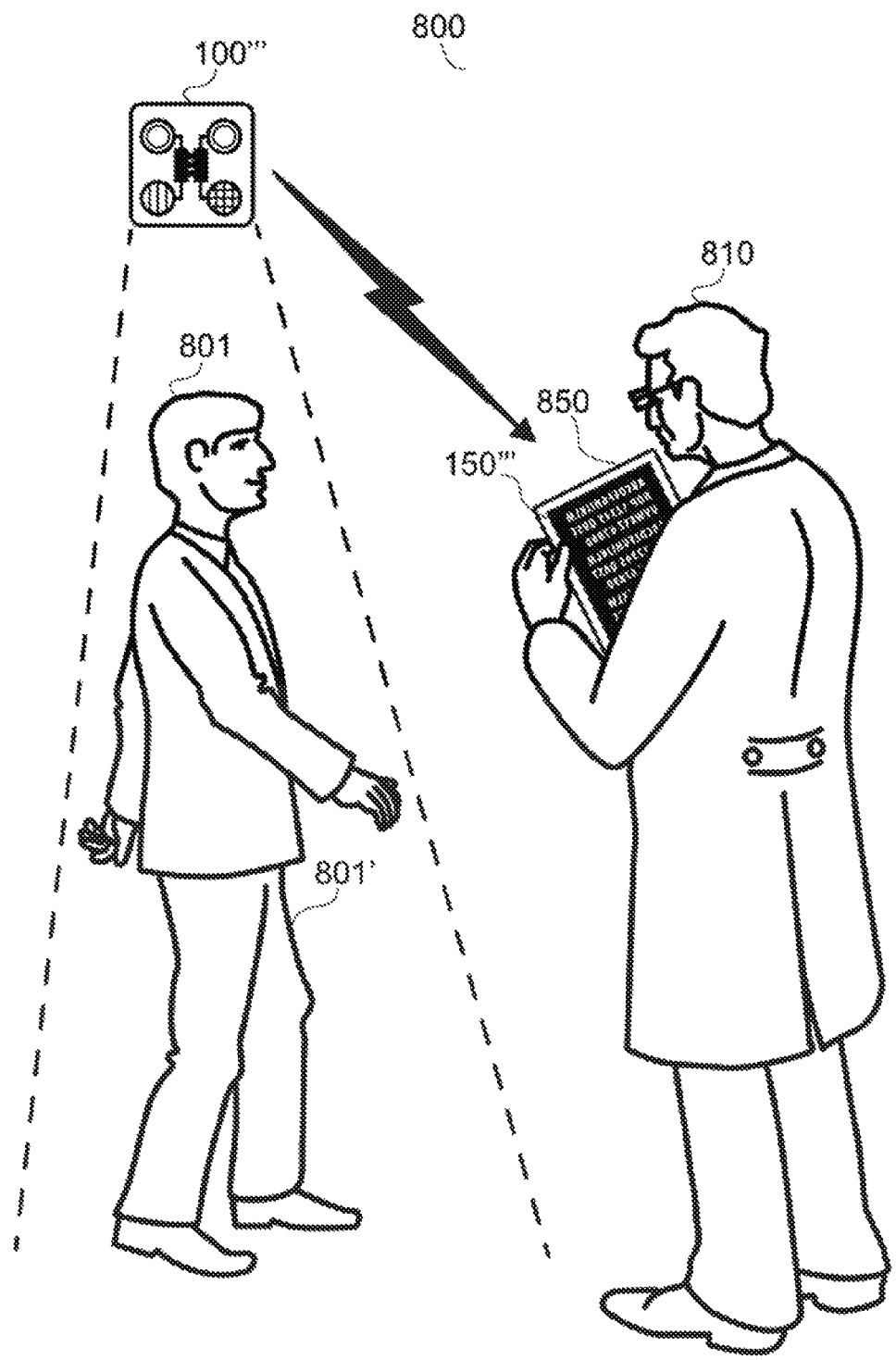
FIG. 8A-B depict examples of a transcription of a person's appearance to text during (medical) examination.
Figure 8B:
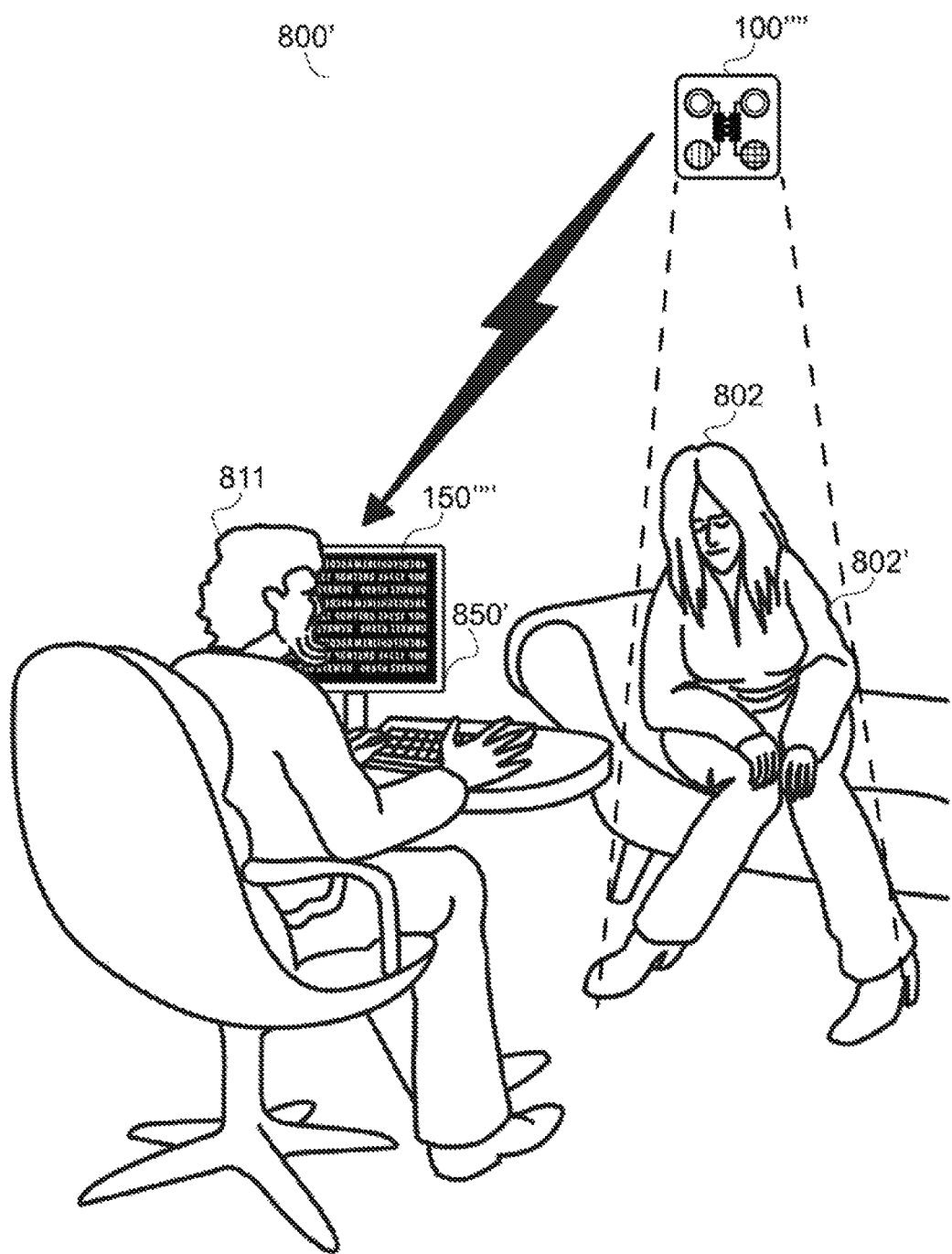

FIGS. 8A-B in general depict examples of a transcription of a person's appearance to text during (medical) examination.

FIG. 8A depicts an example 800 wherein a patient 801 is examined by a doctor 810, and wherein the doctor 810 is assisted by an example embodiment of a device 100'''. The patient 801 makes a view steps while device 100''' detects an appearance 801' (e.g. a stiff leg) of patient 801 and transcribes the appearance 801' to a text 150''', and outputs the text 150''' to a tablet device 850. In this example a software application on the tablet device 850 allows the doctor 810 to adjust (e.g. modify, delete and add text) the text 150 in order to fulfil his requirements before saving the text 150 in a medical record of patient 801.

In another example a doctor 810 cannot adjust a text 150. As such the output text 150, not modified by doctor 810, will intrinsically be more objective and reflect a description of an appearance 801' of patient 801 as a result of a transcription by device 100''' without a noise of a doctor's subjective observation. In particular when patient 801 is being examined periodically by possibly different doctors this contributes systematically to more objective, and likely more reliable, documentation. At the end such documentation can help a doctor to conclude whether the condition of patient 801 has been improved or deteriorated. This allows a doctor to adapt and adjust a therapy for patient 801.

In further example, an example embodiment of a device 100''' is used in clinal trials wherein it is crucial to document participants' appearances in an objective manner; for instance, before and after a new treatment, such as a treatment with a novel vaccine, drug, dietary choice, dietary supplement, and/or medical device.

In an embodiment of a device 100''' a text 150''' is transcribed in compliance with a document model such as SOAP (subjective, objective, assessment, and plan) or OODA (Observe Orient Decide Act).

FIG. 8B depicts an example 800' wherein a client 802 is in a therapy session with a psychiatrist 811, and wherein the psychiatrist 811 is assisted by an example embodiment of a device 100''''. During the therapy session device 100'''' detects and transcribes client's appearances 802' to text 150'''', and outputs the text 150'''' to a computer device 850.

Similar to the description in FIG. 8A the transcription (i.e. 150'''') can either be adjusted by the psychiatrist 811 or left unchanged.

This allows automated documentation of the appearances 802' of client 802 that could be used for further diagnosis's or scientific research. In this context the computer readable medium may include a non-transitory computer readable medium, for example, such as computer-readable media that stores data for short periods of time like register memory, processor cache and Random Access Memory (RAM). The computer readable medium may also include non-transitory media or memory, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, a tangible storage device, or other article of manufacture, for example.

The embodiments described earlier can be combined with any of the aforementioned methods described.

It will also be clear that the above description and drawings are included to illustrate some embodiments of the invention, and not to limit the scope of protection. Starting from this disclosure, many more embodiments will be evident to a skilled person. These embodiments are within the scope of protection and the essence of this invention and are obvious combinations of prior art techniques and the disclosure of this patent.

What is claimed is:

1. A medical device configured to transcribe an appearance of a human being, said device comprising:

a common housing holding:

an image capturing sensor;

a computing device comprising a data processor and a computer program product comprising:

a first machine learning model trained for detecting and labeling human beings in at least one image;

a second machine learning model trained for detecting appearances of human beings in at least one image;

a transcription module configured to transcribe the detected appearances of human beings to text, wherein said computer program product when running on said data processor causes said computing device to:

retrieve at least one image from said image capturing sensor;

analyze said at least one image, wherein analyzing comprises inputting said at least one image to said first machine learning model said first machine learning model detecting presence of a human being in said at least one image and said first machine learning model labeling the detected human being in said at least one image using a label;

input at least a part of said at least one image to said second machine learning model, said part of said at least one image comprising the labeled human being, and said second machine learning model providing said appearance of said labeled human being as an output; and apply said transcription module to transcribe the retrieved appearance of said labeled human being to text and outputs said text, wherein the transcription to text in said transcription module involves creating a medical record and output said text into said medical record; and said second machine learning model comprising:
- a first deep neural network which captures the skeleton data of said human being in said at least a part of said at least one image, said first deep neural network using said at least a part of said least one image as an input and outputs said skeleton data;
- a second deep neural network which captures a first appearance of said human being, said second deep neural network using said skeleton data from said first deep neural network as an input and outputs said first appearance in first appearance data;
- a third deep neural network which captures a second appearance of said human being in said at least a part of said at least one image, said third deep neural network using said at least a part of said at least one image as an input and outputs said second appearance in second appearance data, and
- a fourth deep neural network which captures a third appearance of said human being using said first and second appearance data as an input and outputs third appearance data, said third appearance data comprising a prediction of probabilities of said appearance.

2. The device according to claim 1, wherein said device is configured to transcribe said appearance of at least one human being within a plurality of human beings, wherein said analyzing comprises:
- said first machine learning model detecting presence of said plurality of human beings in said at least one image;
- said first machine learning model labeling said at least one human being within the detected plurality of human beings in said at least one image using a label;
- retrieving at least a part of said at least one image, said part of said at least one image comprising the labeled at least one human being within said detected plurality of human beings, resulting in at least one labeled image;
- inputting said at least one labeled image to said second machine learning model, and
- retrieving said appearance of said labeled at least one human being within said detected plurality of human beings from said second machine learning model as output.

3. The device according to claim 1, wherein said device is configured to transcribe multiple appearances of said labeled human being, and said computer program product when running on said data processor causes said computing device to:
- receive multiple images from said image capturing sensor;
- analyze said multiple images, the analyzing comprises:
- input said multiple images to said first machine learning model; said first machine learning model detecting presence of said human being in a first image of said multiple images; said first machine learning model labeling the detected human being in said first image of said multiple images with said label;
- retrieve at least a part of said first image of said multiple images, said part of said first image of said multiple images comprising the labeled human being, resulting in a labeled first image; said first machine learning model detecting presence of said labeled human being in every further image of said multiple images; said first machine learning model labeling said detected human being in every further image of said multiple images with said label; retrieving at least a part of said every further image of said multiple images, said part of said every further image of said multiple images comprising said labeled human being, resulting in a labeled set of further images;
- input said labeled first image and said labeled set of further images to said second machine learning model,
- retrieve said multiple appearances of said labeled human being from said second machine learning model;
- apply said transcription module to transcribe the retrieved multiple appearances, of said labeled human being, to text, and
- output said text.

4. The device according to claim 3, wherein said analyzing comprises:
- inputting a first image of said multiple images to said first machine learning model; said first machine learning model detecting presence of said human being in said first image of said multiple images; said first machine learning model labeling the detected human being in said first image of said multiple images with said label;
- retrieving at least a part of said first image of said multiple images, said part of said first image of said multiple images comprising the labeled human being, resulting in a labeled first image;
- inputting a further image of said multiple images to said first machine learning model; said first machine learning model detecting presence of said labeled human being in said further image of said multiple images; said first machine learning model labeling said detected human being in said further image of said multiple images with said label;
- retrieving at least a part of said further image of said multiple images, said part of said further image of said multiple images comprising said labeled human being, resulting in a labeled further image;
- inputting said labeled first image and said labeled further image to said second machine learning model, and
- retrieving said multiple appearances of said labeled human being from said second machine learning model.

5. The device of claim 1, wherein said device is configured to transcribe said appearance of each human being within a plurality of human beings, wherein said analyzing comprises:
a) said first machine learning model detecting presence of a plurality of human beings in said at least one image;
b) said first machine learning model labeling the detected plurality of human beings in said at least one image using a label for each detected human being;
c) retrieving at least one of the labeled human beings, resulting in a set of retrieved human beings;
d) inputting at least a part of said at least one image, said part of said at least one image comprising at least one being of said set of retrieved human beings, to said second machine learning model,
e) retrieving said appearance of said labeled human beings in said set of retrieved human beings from said second machine learning model, and
f) repeating said c), d) and e) until said appearance of each human being within a plurality of human beings is retrieved, wherein said computer program product when running on said data processor causes said computing device to:

apply said transcription module to transcribe the retrieved appearances of said each human being within a plurality of living beings to text, and output said text.

6. The device according to claim 1, wherein:
said skeleton data comprises a k-dimensional vector;
said first appearance data comprises an n-dimensional first appearance vector;
said second appearance data comprises an m-dimensional second appearance vector, and
said third appearance data comprises a p-dimensional third appearance vector, wherein said second machine learning model further comprises:
a concatenation module which concatenate said m-dimensional second appearance vector and said n-dimensional first appearance vector into a (m+n)-dimensional intermediate vector.

7. The device according to claim 1, wherein said computer program product causes said computing device to receive multiple images providing a time series of images, input said multiple images in said second machine learning model providing a series of said third appearance data, concatenate said series of third appearance data and provide the concatenated output as input for a further deep neural network to predict probabilities of each appearances of the labeled human being present in said time series of images.

8. The device of claim 1, wherein said multiple images comprise a time base, in an embodiment said multiple images comprise a part of a video recording or a series of time-laps images.

9. The device of claim 1, wherein said multiple images comprise a real-time processed video recording.

10. The device of claim 1, wherein said appearance comprises a pose.

11. The device of claim 1, wherein said appearances comprises a series of poses or a change of poses, said series of poses or change of poses defining at least one action.

12. A computer program product comprising a non-transitory computer readable medium and for running on a computing device of a medical device configured to transcribe an appearance of a human being, wherein said medical device comprises a common housing holding:
an image capturing sensor;
said computing device comprising a data processor, wherein said computer program product comprises:
a first machine learning model trained for detecting and labeling human beings in at least one image;
a second machine learning model trained for detecting appearances of human beings in at least one image;
a transcription module to transcribe the detected appearances of human beings to text;
and said computer program product when running on said data processor, causes said computing device to:
receive at least one image from said image capturing sensor;
analyze said at least one image, the analyzing comprises:
input said at least one image to said first machine learning model;
retrieve from said first machine learning model a presence of a human being in said at least one image;
retrieve a label from said first machine learning model of the detected human being in said at least one image;
input at least a part of said at least one image, said part of said at least one image comprising the labeled human being, to said second machine learning model;
retrieve said appearance of said labeled human being from said second machine learning model;
apply said transcription module to transcribe the retrieved appearance of said labeled human being to text, and
output said text, wherein the transcription to text in said transcription module involves creating a medical record and output said text into said medical record; and
said second machine learning model comprising:
a first deep neural network which captures the skeleton data of said human being in said at least a part of said at least one image, said first deep neural network using said at least a part of said at least one image as an input and outputs said skeleton data;
a second deep neural network which captures a first appearance of said human being, said second deep neural network using said skeleton data from said first deep neural network as an input and outputs said first appearance in first appearance data;
a third deep neural network which captures a second appearance of said human being in said at least a part of said at least one image, said third deep neural network using said at least a part of said at least one image as an input and outputs said second appearance in second appearance data, and
a fourth deep neural network which captures a third appearance of said human being using said first and second appearance data as an input and outputs third appearance data, said third appearance data comprising a prediction of probabilities of said appearance.

* * * * *